Figure 1:
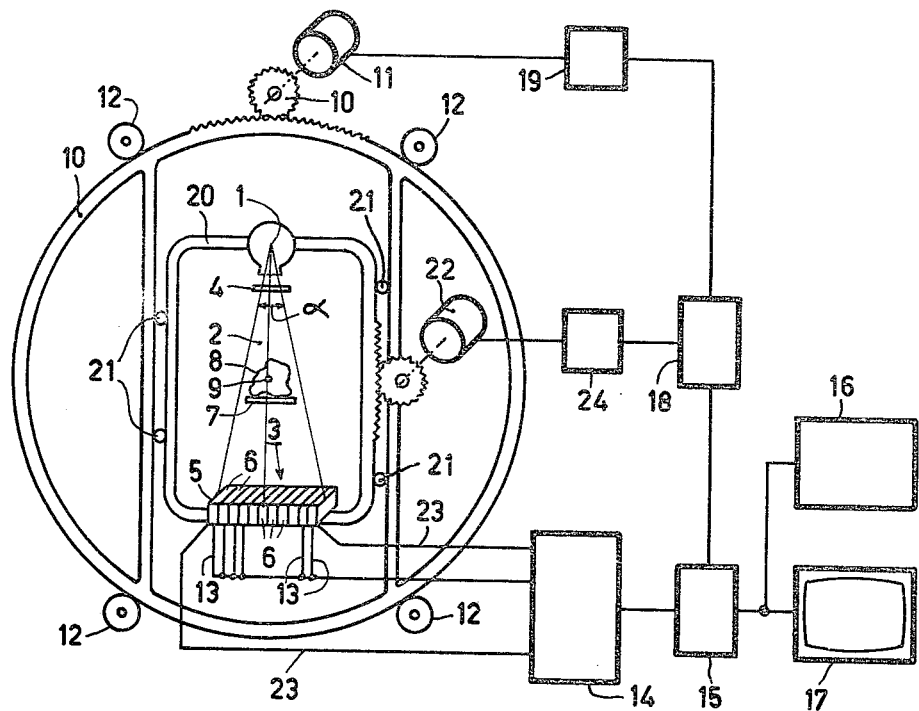

United States Patent [19]

Zonneveld

[11] 4,134,020

[45] Jan. 9, 1979

[54] APPARATUS FOR MEASURING LOCAL ABSORPTION DIFFERENCES

[75] Inventor: Frans W. Zonneveld, Eindhoven, Netherlands

[73] Assignee: U.S. Philips Corporation, New York, N.Y.

[21] Appl. No.: 836,684

[22] Filed: Sep. 26, 1977

[30] Foreign Application Priority Data

Oct. 1, 1976 [NL] Netherlands .................. 7610858

[51] Int. Cl.² ........................................... G03B 41/16
[52] U.S. Cl. .............................. 250/445 T; 250/523
[58] Field of Search ............... 250/439 R, 444, 445 R, 250/445 T, 446, 447, 448, 449, 490, 523

[56] References Cited

U.S. PATENT DOCUMENTS 3,922,552  11/1975  Tedley .................. 250/445 T

Primary Examiner—Craig E. Church
Attorney, Agent, or Firm—Thomas A. Briody; Jack E. Haken

[57] ABSTRACT

The radiation source of a fan-beam X-ray scanner is adjustable relative to the body to be examined so that the beam exactly covers the body. Use can be made of the radiation which passes besides the body for adjustment of the optimum distance. The variation of the enlargement factor which is caused by adjustment is recorded and is applied to an arithmetic unit for use in calculating the absorption values.

6 Claims, 2 Drawing Figures

APPARATUS FOR MEASURING LOCAL ABSORPTION DIFFERENCES

The invention relates to apparatus for determining local absorption differences in a body, comprising a radiation source for generating a fan-shaped beam of radiation which irradiates the body, a detector which is location-sensitive in at least one direction, and a scanning mechanism, the radiation source and the detector always being situated opposite each other, one on each side of a central axis through the body to be examined. Such apparatus will be referred to herein as apparatus of the kind referred to.

Apparatus of this kind is known, for example from U.S. Pat. No. 3,940,626 in the name of Hounsfield, dated Feb. 24th, 1976. This specification describes apparatus for the examination of the human body by means of a fan-shaped flat beam of X-rays, that is to say a beam which diverges in one direction — the width direction — and which is parallel in a direction transverse thereto, i.e. the thickness direction. For the detection of radiation after passage through the body, use is made of a series of separate detector elements, said series covering a width which corresponds to the local width of the radiation beam. When apparatus of this kind is used for alternately examining different parts of the body, there is a drawback in that, for example, after a large part of the body has been completely covered, the beam will extend beyond the boundary of a smaller part of the body to be subsequently irradiated. This can be prevented by adaptating of the opening angle of the radiation beam to the width of the body. However, such a beam adaptation is accompanied by a loss of relative resolution, because a smaller object will be irradiated by only part of the radiation beam and a correspondingly smaller number of detector elements will receive radiation.

The invention has for an object to provide improved apparatus of the kind referred to in which this drawback can be mitigated. In accordance with the invention there is provided apparatus for determining local absorption differences in a body, comprising a radiation source for generating a fan-shaped beam of radiation which irradiates the body, detector means which is location-sensitive in at least one direction, a scanning mechanism, the radiation source and the detector means always being situated opposite each other one on each side of a central axis through the body to be examined, and means for adjusting the distance between a central axis through the body to be examined and the radiation source and/or the detector means to adapt the beam width in the region occupied by the body to a relevant dimension of the body.

In one embodiment of the invention, the radiation source emits a flat fan-shaped beam which completely covers the body to be examined in one direction, a holder which supports the radiation source and the detector being displaceable in a direction transverse to a central axis through the body to be examined. In an embodiment of the invention, the position of the holder is adjusted automatically by a signal which originates from detector elements exposed to radiation passing to the side of the body at the boundaries of the fan-shaped beam.

Figure 2:
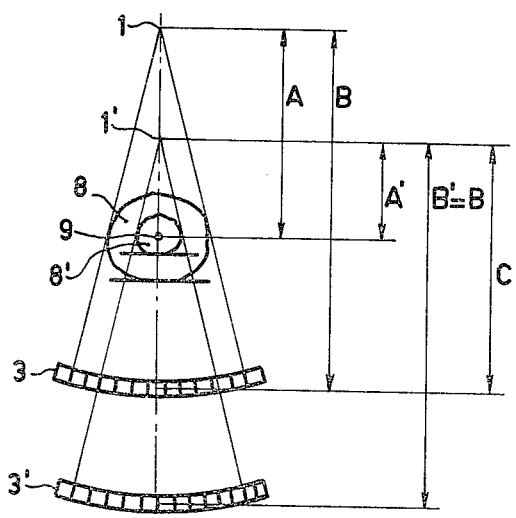

In order that the invention may be clearly understood and readily carried into effect embodiments thereof will now be specifically described by way of example, with reference to the accompanying drawing, of which:

FIG. 1 is a diagrammatic representation of apparatus embodying the invention, and comprising a displaceable holder which supports the source and the detector, and FIG. 2 is a diagram illustrating various locations of the detector and radiation source combination relative to a body to be examined.

A scanning X-ray examining apparatus as diagrammatically shown in FIG. 1 comprises a radiation source 1 which preferably consists of an X-ray tube, but which may alternatively consist of, for example, a radioactive isotope with an effective natural radiation, such as Am 241 or Gd 153. The intensity of an X-ray beam 2 emitted by the radiation source 1 is locally measured by a detector 3. The radiation source in this case forms a fan-shaped beam having an opening angle $\alpha$. Viewed in a direction transverse to the plane of the drawing, the beam is at least in principle parallel and has a small thickness of, for example, 3 to 15 mm in this direction. In order to form a beam of this kind, a slot-like diaphragm 4 is added. The thickness dimension 5 of the detector elements, i.e. the dimension thereof transverse to the plane of the drawing, can be adapted to the beam thickness.

In practice, the beam will diverge to some extent in the thickness direction, i.e. transverse to the plane of the fan, and this results in a corresponding detector dimension which is larger in this direction than the beam thickness in the region of the body to be examined. The width dimension of the detector elements 6 and their spacing determines the number of detector elements and hence the resolution within a given beam angle of the fan-shaped beam. The detector is in this case composed of, for example, approximately 300 separate detector elements with a centre-to-centre distance of, for example, 5 mm. However, use can alternatively be made of an homogeneous detector, for example, a gas-filled detector including a series of individual local detection electrodes. A support table 7 for a body 8 to be examined can be displaced along an isocentric axis 9 in the longitudinal direction, the source/detector system being rotatable around the body by means of a toothed ring 10 which is driven by a motor 11 and which is supported by guides 12. Moreover, the source/detector system is preferably tiltable about an axis extending transversely to the isocentric axis, the source and the detector then moving out of the plane of the drawing in opposite directions, with reference to the drawing.

The signals to be measured can be individually applied from each of the detector elements 6 via connections 13, to an amplifier/convertor 14 in which the signals of each of the detectors can be individually amplified, corrected and converted. Output signals from the amplifier/convertor 14 are applied to an arithmetic device 15 in which the local absorption is calculated from the collected signals. The absorption values thus obtained can be stored in a recording device 16 and displayed on a monitor 17, for example, for a selected slice of the body. Devices of this kind are generally known and no further detailed description of the construction is required in this context. A control device 18 is provided for the control and synchronization of the displacements and detection processes. The control device 18 includes an on-off switch and interrelates the time of arrival of measurement signals with the position of the source/detector system relative to the body. The rotation of the system is adjusted and recorded via a control unit 19. In the present embodiment, as is diagrammatically shown, the source/detector system is slidable relative to the axis 9 since a support frame 20, supporting the source and the detector, is displaceable along guides 21 by means of a drive motor 22. If the body has a transverse dimension, as shown, which is such that boundary rays at the edge of the beam 2 reach the detectors unobstructed by the body 8, signals are derived therefrom and applied to the preamplifier/converter unit 14. By means of a signal formed thereby, a control device 24 for the displacement of the support frame 20 is activated and a correct adaptation of the arithmetic unit is realised via this unit and the control unit 18. The source 1 is then displaced towards the body 8, by the motor 22 until the control signal attains a residual value which can be adjusted; so that, for example, only a single outer detector element is exposed to direct radiation at each side of the body. If the signal is lower than the residual value after positioning a body in the apparatus, the process is carried out with respect to displacing the support frame 20 in the opposite direction. When the source has been displaced in the indicated direction, a change will occur in the enlargement factor relating to the measurement, as can be deduced from FIG. 2. This change should, of course, be taken into account when carrying out the calculation of the absorption values, and for this purpose the displacement mechanism is coupled to the arithmetic unit.

FIG. 2 shows two different positions of the source/detector system relative to a body to be measured. For a comparatively large body 8, the source 1 is situated at a distance A from the body, i.e. from the isocentric axis 9. For a comparatively small body 8', the souce 1' is situated at a distance A' therefrom. In the present embodiment, the distance between the source and the detector is fixed, so that B = B'. Therefore, the enlargement factor for the large body is given by the ratio of B to A, and for the small body by the ratio of B to A', so that in the latter case it is substantially greater.

In the case of an optimum adjustment for the body to be measured, the relative resolution in the direction of fan is constant, because the same number of discrete detector elements is always present within a fixed beam angle. By adjustment of the width of the aperture set by the diaphragm 4 in the direction perpendicular to the fan plane, i.e. the dimension in the direction of the beam thickness, the resolution in this direction can be adjusted, if desired, to the various displacement positions.

It is alternatively possible to arrange only one of the two elements of the source/detector system to be displaceable relative to the axis 9. In that case it is not possible to achieve a constant relative resolution, however a more limited adaptation is possible. Assuming the use of all except the two terminal detectors for a body of maximum permissible width, if the source alone is displaced then, for a given fan angle, fewer detector elements would be used in the case of a narrower body, but the enlargement factor, now given by the ratio of C and A', will become greater as the body becomes smaller. Upon displacement of the detectors alone, a position can normally be found in which all except the two terminal detectors are used. However, overradiation will then occur, so that the described adjustment criterion is difficult to employ and only part of the entire beam will be used. In order to utilize a radiation dose which is optimum for detection in the case of measurements carried out at different enlargements, the intensity of the radiation source is preferably adjusted in dependence on the geometry of the arrangement. In an embodiment of the invention, the intensity of the radiation beam emitted by the source is automatically adjusted in correspondance with a change of the enlargement factor. For the adaptation of the radiation intensity to the enlargement factor, use can be made of a filter which is to be added per step of the enlargement. For the adaptation of the radiation intensity, a preferred embodiment utilizes the adjusting device described in allowed U.S. patent application Ser. No. 642,159 notably the pulse-width control system described therein is suitable for adapting the tube output intensity to the tube-patient distance.

What is claimed is:

1. Apparatus for determining local absorption differences in a body, comprising a radiation source for generating a fan-shaped beam of penetrating radiation which irradiates the body, detector means which are location-sensitive in at least one direction, scanning means for orbiting said source and detector means about a central axis which passes through said body, the radiation source and the detector means always being situated opposite each other, one on each side of said central axis, and means for adjusting the distance between said central axis and the radiation source and/or the detector means to which adapt the beam width in the region occupied by the body to a relevant dimension of the body.

2. Apparatus as claimed in claim 1, in which the radiation source and the detector are displaceable together along an axis connecting the radiation source with the detector means.

3. Apparatus as claimed in claim 1, in which one element of an assembly system formed by the combination of the radiation source and the detector means can be separately displaced along an axis connecting the radiation source with the detector means.

4. Apparatus as claimed in claim 1, further, including means for automatically adjusting the distance between the radiation source and the body to an optimum.

5. Apparatus as claimed in claim 1, further including detectors means for measuring radiation which has not passed through the body and for adjusting the position of the radiation source relative to the body in response to said measuring.

6. Apparatus as claimed in claim 1, further including adjustment means which function to control the intensity of the beam emitted by the radiation source in a manner dependent on the distance between the source and the body.

* * * * *

UNITED STATES PATENT AND TRADEMARK OFFICE
CERTIFICATE OF CORRECTION

PATENT NO. : 4,134,020
DATED : January 9, 1979
INVENTOR(S) : FRANS W. ZONNEVELD

It is certified that error appears in the above-identified patent and that said Letters Patent are hereby corrected as shown below:

Claim 1, line 12, delete "to"

Signed and Sealed this

Second Day of October 1979

[SEAL]

Attest:

RUTH C. MASON
Attesting Officer

LUTRELLE F. PARKER
Acting Commissioner of Patents and Trademarks